United States Patent
Steele et al.

(10) Patent No.: US 9,402,674 B2
(45) Date of Patent: Aug. 2, 2016

(54) SURGICAL INSTRUMENT WITH PLANETARY GEAR SYSTEM

(71) Applicant: WARSAW ORTHOPEDIC, INC., Warsaw, IN (US)

(72) Inventors: Bradley E. Steele, Germantown, TN (US); Thomas V. McGahan, Memphis, TN (US); Jacob R. Zimmermann, North Little Rock, AR (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 56 days.

(21) Appl. No.: 14/174,418

(22) Filed: Feb. 6, 2014

(65) Prior Publication Data
US 2014/0155907 A1  Jun. 5, 2014

Related U.S. Application Data

(62) Division of application No. 12/915,861, filed on Oct. 29, 2010, now Pat. No. 8,696,511.

(51) Int. Cl.
| | |
|---|---|
| *A61B 17/16* | (2006.01) |
| *A61B 17/88* | (2006.01) |
| *A61B 17/70* | (2006.01) |
| *B25B 15/00* | (2006.01) |
| *B25B 17/02* | (2006.01) |

(52) U.S. Cl.
CPC ......... *A61B 17/8877* (2013.01); *A61B 17/7082* (2013.01); *A61B 17/8875* (2013.01); *B25B 15/001* (2013.01); *B25B 17/02* (2013.01); *A61B 17/8894* (2013.01)

(58) Field of Classification Search
CPC .................................................. A61B 17/1624
See application file for complete search history.

(56) References Cited

U.S. PATENT DOCUMENTS

| | | | | |
|---|---|---|---|---|
| 3,797,497 A | * | 3/1974 | Crim | A61B 17/1617 606/173 |
| 4,728,876 A | * | 3/1988 | Mongeon | A61B 17/1624 310/50 |
| 4,736,742 A | * | 4/1988 | Alexson | A61B 17/1624 408/124 |
| 5,207,697 A | * | 5/1993 | Carusillo | A61B 17/1626 320/115 |
| 5,226,906 A | | 7/1993 | Crombie et al. | |
| 5,433,721 A | * | 7/1995 | Hooven | A61B 17/072 227/175.1 |
| 5,863,272 A | | 1/1999 | Anderson | |
| 5,993,454 A | * | 11/1999 | Longo | A61B 17/1624 606/80 |
| 6,110,174 A | | 8/2000 | Nichter | |
| 6,312,441 B1 | | 11/2001 | Deng | |
| 6,663,641 B1 | | 12/2003 | Kovac et al. | |

(Continued)

FOREIGN PATENT DOCUMENTS

WO    2007121271 A2    10/2007

*Primary Examiner* — Tisha Lewis

(57) ABSTRACT

A surgical instrument for applying a rotational force to a structural element during a surgical procedure. The instrument may be designed for increasing an input force to produce an enlarged output force adequate for fracturing an excess section of the elongated element from a remainder of the structural element. The instrument may include an input mechanism that receives an external rotational input force, a planetary gear system that multiples the input force, and an output mechanism that attaches to and delivers the multiplied rotational output force to the excess section of the structural element. The output mechanism may also be configured to capture the separated excess section. The instrument may include a housing and a handle for grasping and manipulating during the surgical procedure.

20 Claims, 8 Drawing Sheets

(56) References Cited

U.S. PATENT DOCUMENTS

| | | |
|---|---|---|
| 6,675,911 B2 | 1/2004 | Driessen |
| 6,824,495 B1 | 11/2004 | Kirschner |
| 6,866,607 B2 | 3/2005 | Nishiji et al. |
| 6,958,071 B2 | 10/2005 | Carusillo et al. |
| 7,021,399 B2 | 4/2006 | Driessen |
| 7,448,869 B2 * | 11/2008 | Kuhn ............... A61B 17/1624 433/105 |
| 2002/0107525 A1 | 8/2002 | Harari et al. |
| 2006/0265006 A1 | 11/2006 | White et al. |
| 2007/0121271 A1 | 5/2007 | Kim et al. |
| 2007/0270859 A1 | 11/2007 | Companioni et al. |
| 2008/0221583 A1 | 9/2008 | Sharifi-Mehr et al. |
| 2008/0243123 A1 | 10/2008 | Gordils Wallis et al. |
| 2009/0090764 A1 | 4/2009 | Viola |
| 2009/0270880 A1 | 10/2009 | Gale et al. |
| 2009/0287203 A1 * | 11/2009 | Mazzone ........... A61M 25/1038 606/21 |
| 2010/0076461 A1 | 3/2010 | Viola et al. |

* cited by examiner

SURGICAL INSTRUMENT WITH PLANETARY GEAR SYSTEM

This application is a divisional application of co-pending U.S. patent application Ser. No. 12/915,861 filed Oct. 29, 2010, the entire disclosure of which is herein incorporated by reference into the present application.

BACKGROUND

The present application is directed to surgical instruments for applying a rotational force to an element and, more particularly, to a surgical instrument with a planetary gear system.

Various types of structural elements are used in patients during surgical procedures. Examples include but are not limited to rods such as for attaching to vertebral members or to a broken femur, bone anchors for attaching an elongated element to a bone, pins for attaching together bones or bone sections, and posts for attaching to bones and/or tissue. It is often necessary to remove sections of the structural elements, such as a head of a set screw or an excess length of a rod. Many times the removal occurs after the structural elements have been inserted into a patient. Various instruments are presently used for removing the excess sections. However, the instruments have various drawbacks that add complexity to the surgical procedure.

Some of the previous instruments have a relatively large size. The large size is necessary to generate an adequate force to remove the excess section from the remainder of the structural member. One example is an instrument with large lever arms. The large lever arms are necessary for the instrument to create an adequate shearing force, but the large sizes make the instruments difficult to use in small surgical sites. Further, the instruments may be too large to reach the needed area within the surgical site where the section is to be removed from the remainder of the structural member.

Other instruments are uncontrollable at the time the section is removed. This is caused by the relatively large force necessary to remove the section and the release of the force at the moment of removal. The force release may cause the instruments to "jump" or "buck" making it difficult to control for the medical practitioner. The force release may also cause a shock to the patient.

SUMMARY

The present application is directed to surgical instruments for applying a rotational force to a structural element. The surgical instrument may include a housing, and may include an input member partially positioned in the housing and may include an input portion that extends outward from the housing. The input member may be rotatable relative to the housing, and may include a sun gear. An output shaft may be partially positioned in the housing and may include a length to extend outward from the housing and has a receptacle configured to engage with the element. The elongated output shaft may be rotatable relative to the housing. A planetary gear system may be positioned in the housing and may include a sun gear, planet gears that engage with and rotate around the sun gear, and an annular ring gear that extends around the sun gear and the plurality of planet gears. The ring gear may include interior teeth that engage with the planet gears. The planet gears may be rotatable relative to the housing and the ring gear may be non-rotatable relative to the housing. The input member, the output shaft, and the planetary gear system may be operatively connected for rotation of the input member in a first rotational direction resulting in rotation of the output shaft in the first rotation direction.

The surgical instrument may include an elongated input member and may be aligned with a longitudinal axis of the instrument and have a distal end with a sun gear with first teeth and an opposing proximal end. A drive member may be positioned at the distal end of the input member and may include mounts that face towards the input member and fingers that extend outward away from the input member. Each of the mounts and the fingers may be positioned radially outward from the longitudinal axis. Planet gears may be attached to the drive member and each may include second teeth that mesh with the first teeth of the sun gear. Each one of the planet gears may be attached to one of the mounts for the planet gears to rotate relative to the drive member and also remain at fixed points on the drive member. Each of the planet gears may be positioned radially outward from the longitudinal axis. A ring gear with an annular shape and an inner surface with third teeth may engage with the second teeth of the planet gears. An output member may be aligned with the longitudinal axis and may include an elongated shape with a first end and second end. The first end may include arms spaced apart by gaps that receive the fingers on the drive member. The second end may include a mount configured to engage the element. The input member, the drive member, and the output member may be operatively connected with rotation of the input member in a first rotational direction resulting in rotation of the output member in the same first rotational direction.

The application also includes a method of removing a section of a structural member that is positioned in a patient. The method may include attaching a receptacle of an output shaft to the section of the structural member that is to be removed. The method may include moving the output shaft axially relative to a planetary gear system and engaging the output shaft with the planetary gear system. The method may include rotating in a first direction an input member that is engaged with the planetary gear system and rotating the planetary gear system. The method may also include rotating the output shaft in the first direction through the planetary gear system and applying a force to the section of the structural member.

The various aspects of the various embodiments may be used alone or in any combination, as is desired.

DETAILED DESCRIPTION

Figure 1:
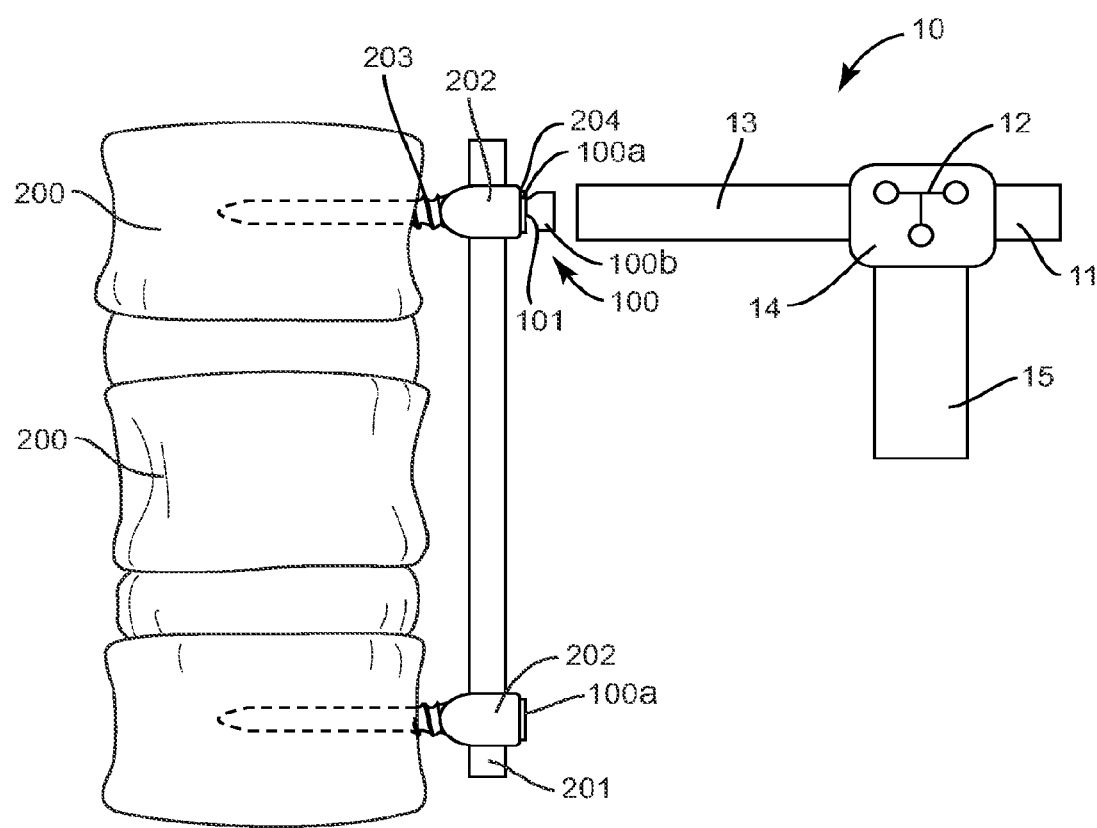
FIG. 1 is a schematic view of an instrument and a fastener attached to bone.

The present application is directed to a surgical instrument for applying a rotational force to a structural element during a surgical procedure. The instrument is designed for increasing an input force to produce an enlarged output force. The enlarged output force is adequate for fracturing an excess section of the elongated element from a remainder of the structural element. As schematically illustrated in FIG. 1, the instrument 10 generally includes an input mechanism 11 that receives an external rotational input force, a planetary gear system 12 that multiples the input force, and an output mechanism 13 that attaches to and delivers the multiplied rotational output force to the excess section of the structural element 100. The applied output force causes an excess section 100b of the structural element 100 to fracture from a section 100a that remains in the patient. The output mechanism 13 may also be configured to capture the separated excess section 100b. The instrument 10 may include an exterior housing 14 with a handle 15 for grasping and manipulating during the surgical procedure.

One example of a structural element 100 acted upon by the instrument 10 is a set screw as illustrated in FIG. 1. The set screw includes a first section 100a that seats within a head 204 of an anchor 202 to capture an elongated element 201 and a second section 100b. The second section 100b of the set screw is necessary for initially positioning and/or initially attaching the first section 100a to the anchor 202. Afterwards, the second section 100b is superfluous and can be removed from the first section 100a. The anchor 202 that receives the set screw also includes a shaft 203 attached to a bone 200.

Figure 2:
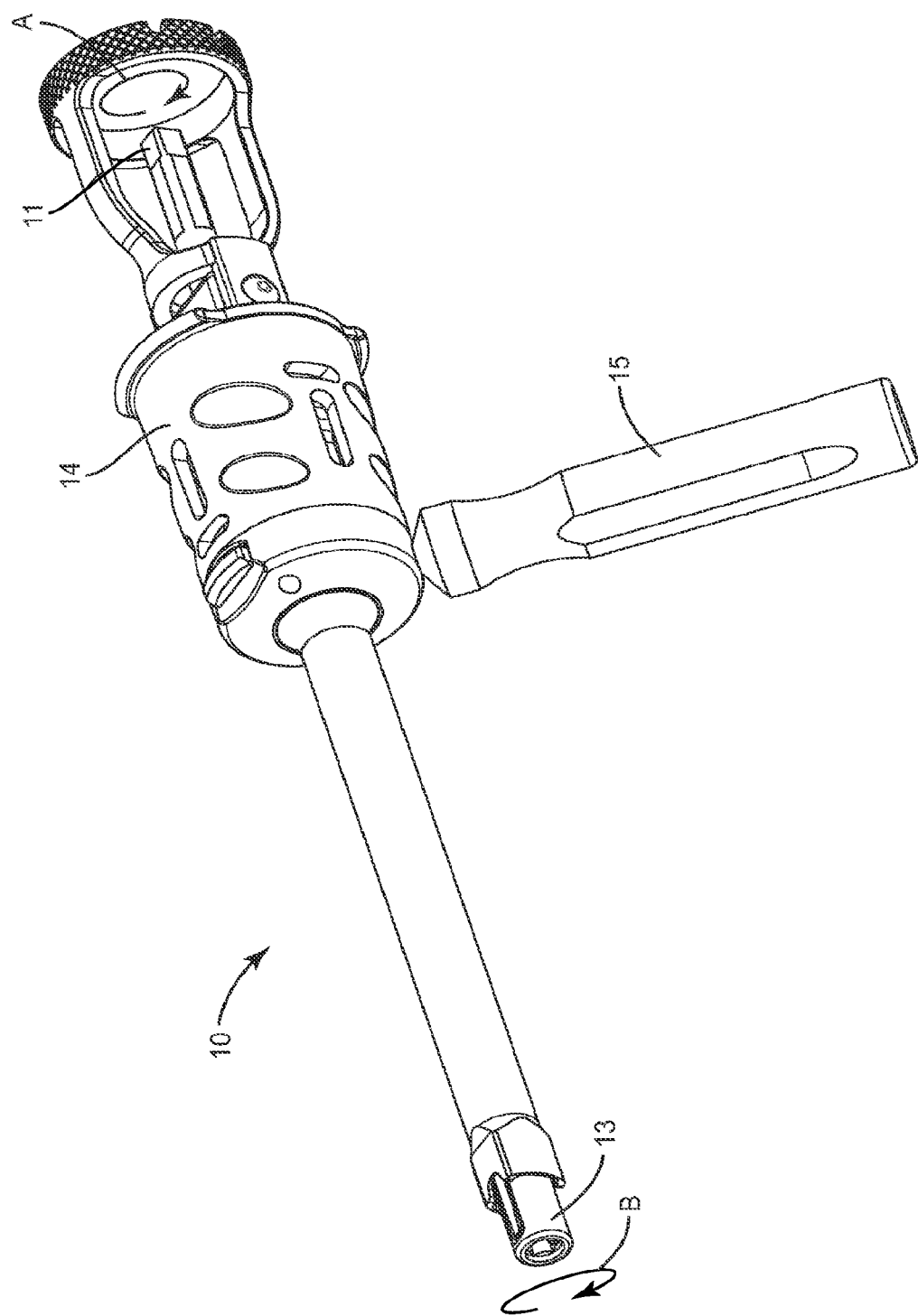
FIG. 2 is a perspective view of an instrument.

FIG. 2 illustrates an exterior view of an instrument 10. The instrument 10 includes the input mechanism 11 that extends outward from a first end of a housing 14, and an output mechanism 13 that extends outward from an opposing second end of the housing 14. The planetary gear system (not illustrated in FIG. 2) is housed within an interior of the housing 14 and operatively connects with the input and output mechanisms 11, 13. A handle 15 may also be located to facilitate use during the surgical procedure. The instrument 10 is configured for rotation A of the input mechanism 11 in a first rotational direction resulting in rotation B of the output mechanism 13 in the same rotational direction.

Figure 3:
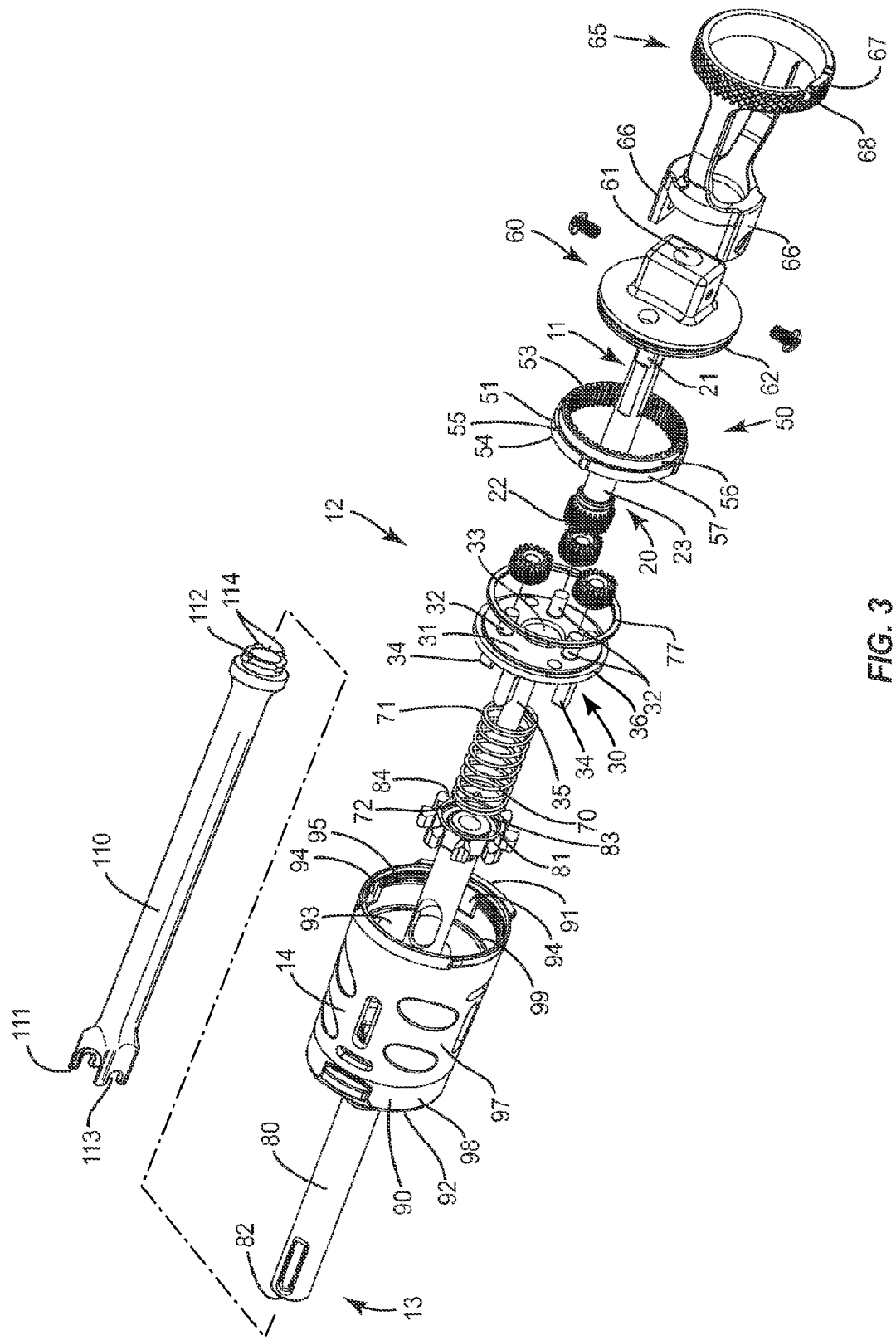
FIG. 3 is an exploded perspective view of an instrument.

FIG. 3 illustrates an exploded view of an instrument 10 that includes the input mechanism 11, the planetary gear system 12, and the output mechanism 13. These elements 11, 12, 13 have a relatively small overall size that facilitates use of the instrument 10 in a surgical setting where it is often necessary to work in a reduced space.

Figure 4:
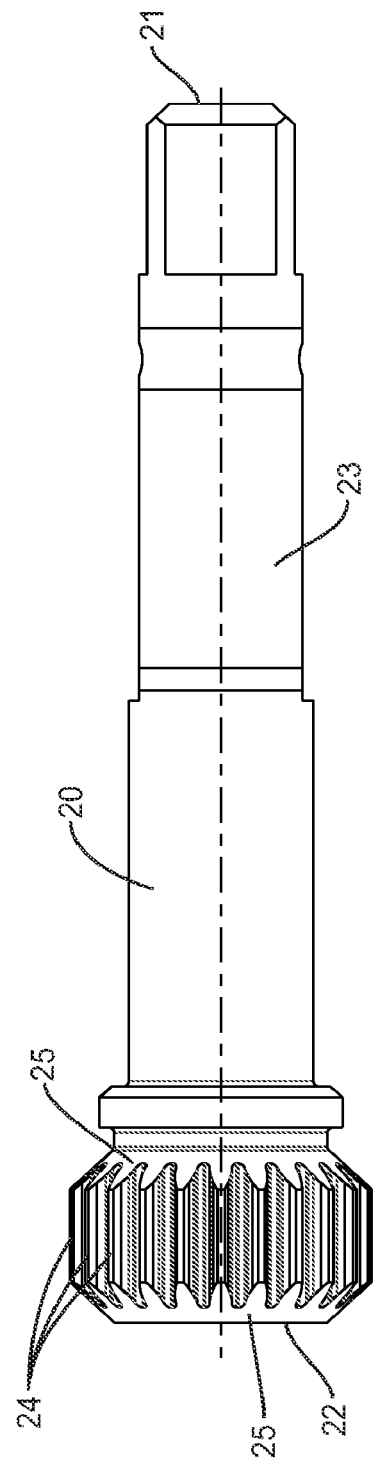
FIG. 4 is a side view of a drive gear.

The input mechanism 11 includes a drive gear 20 positioned at a proximal end of the instrument 10. As more fully illustrated in FIG. 4, the drive gear 20 includes an elongated shape with a proximal end 21, an opposing distal end 22, and an intermediate shaft 23. The proximal end 21 is configured to engage with an external drive force. FIG. 4 illustrates the proximal end 21 with a polygonal cross-sectional shape with a number of flat sides. The flat sides are configured to facilitate receipt of the external input force. The proximal end 21 extends outward beyond the housing 14 (FIG. 2) and is accessible for attachment with the external input force. The length of the drive gear 20 may vary depending upon the instrument 10. In one embodiment, the length between the proximal and distal ends 21, 22 is about 2.25 inches. In another embodiment, the length is about 3.00 inches.

The distal end 22 of the drive gear 20 includes radially-extending teeth 24 that extend outward around the circumference. One or both sides of the teeth 24 may include an angled face 25 positioned at a non-perpendicular angle relative to a longitudinal axis of the shaft 23. In one embodiment, the faces 25 are positioned at opposing angles of about 45° relative to the axis. The drive gear 20 forms the sun gear in the planetary gearing system 12 as will be explained in detail below.

Figure 5:
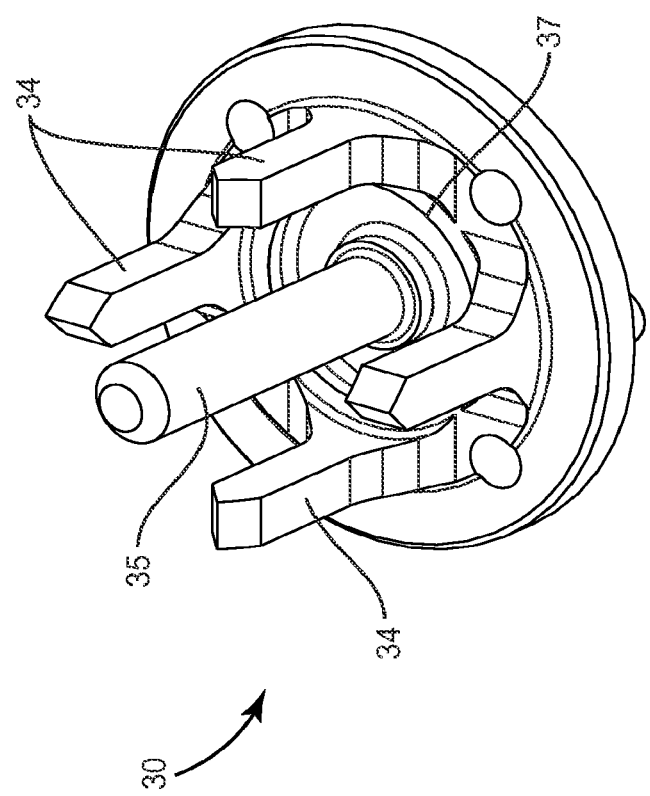
FIG. 5 is a perspective view of a distal side of a drive plate.

A drive plate 30 is positioned at the distal end 22 of the drive gear 20. The drive plate 30 includes a proximal side 31 that faces towards the drive plate 30. FIGS. 3 and 5 include the drive plate 30 having a circular shape and the proximal side 31 being substantially flat. A seat 33 is positioned in the surface of the side 31. The seat 33 may include an indention in the surface sized and shaped to receive the distal end 22. FIG. 3 illustrates the seat 33 with a circular shape and positioned at a center of the side 31.

Posts 32 extend outward from the side 31 in a proximal direction towards the drive gear 20. The posts 32 are straight and may include a circular cross-sectional shape. The lengths of the posts 32 may vary depending upon the size of the gears 40. FIG. 3 includes three posts 32, although other embodiments may include more than three posts 32. One embodiment includes two posts 32 extending outward from the side 31. Another embodiment includes five posts 32. The posts 32 are evenly distributed around a center of the side 31. An embodiment with three posts 32 may include the posts 32 positioned about 120° apart. The posts 32 may each include the same or different cross-sectional shapes and sizes.

The proximal side 31 may also include a shoulder 36 that extends around the periphery. The shoulder is configured to receive a bushing 77 that facilitates rotation of the drive plate 30 relative to a ring gear 50. Bearings may also be positioned between the drive plate 30 and the ring gear 50 to facilitate rotation.

Gears 40 are attached to the drive plate 30 to mesh with the drive gear 20. Each of the gears 40 includes a central aperture 42 that fits over one of the posts 32. The posts 32 maintain the gears 40 at a fixed location on the sides 31 of the drive plate 30. The cross-sectional shapes of the aperture 42 and the posts 32 provide for the gears 40 to rotate about the posts 32. In one embodiment, each has a circular cross-sectional shape. The gears 40 include teeth 41 that extend radially outward and are shaped and sized to mesh with the teeth 24 on the drive gear 20.

A distal side 37 of the drive plate 30 faces away from the drive gear 20. As illustrated in FIG. 5, the distal side 37 includes fingers 34 that extend outward in a distal direction away from the drive gear 20. The fingers 34 are substantially straight and may include various lengths. The fingers 34 may each include one or more flat sides to engage with a gear 84 on a first shaft 80 of the output mechanism 13 as will be explained below. The fingers 34 may include a tapered shape that narrows to a tip to facilitate engagement with the gear 84. The fingers 34 are evenly spaced apart to correspond to the shape of the gear 84. In one embodiment, the drive plate 30 includes four fingers 34, although other embodiments may include different numbers of fingers 34.

A post 35 extends outward in a distal direction from a center of the distal side 37. The post 35 is positioned within an area formed by the fingers 34. The post 35 may include a greater length than the fingers 34 to extend outward a greater distance from the distal side 37. The post 35 may include a circular cross-sectional shape as illustrated in FIG. 5.

A biasing member 70 biases the drive plate 30 away from the first shaft 80 of the output mechanism 13. A proximal end 71 of the biasing member 70 contacts against the distal side 37, and a distal end 72 contacts against a proximal end 81 of the first shaft 80. The biasing member 70 may be a compression spring that maintains the drive plate 30 axially separated from the first shaft 80 when there are no external forces acting on the instrument 10. FIG. 3 illustrates the biasing member 70 being a coil spring with a central channel that extends around the post 35.

An annular ring gear 50 engages with the gears 40. The ring gear 50 includes a central opening sized to extend around the gears 40. The ring gear 50 includes an interior surface 52 with teeth 53 that correspond to the shape and size of the teeth 41 on the gears 40. The teeth 53 extend completely around the interior surface 52.

The ring gear 50 also includes an exterior surface 51 with one or more tabs 54 that extend radially outward away from a center of the ring gear 50. A proximal section 56 of the ring gear 50 may include a smaller diameter than a distal section 57. A shoulder 55 is formed at the intersection of these sections 56, 57. As illustrated in FIG. 3, the tabs 54 may be confined to the distal section 57.

The extent to which the planetary gear system 12 multiplies the input force depends upon the configuration of the gears 40, drive gear 20, and ring gear 50. The multiplication may range from between three to eleven times the input force. In one embodiment, the planetary gear system 12 multiplies the input force by about 3.65.

Figure 6:
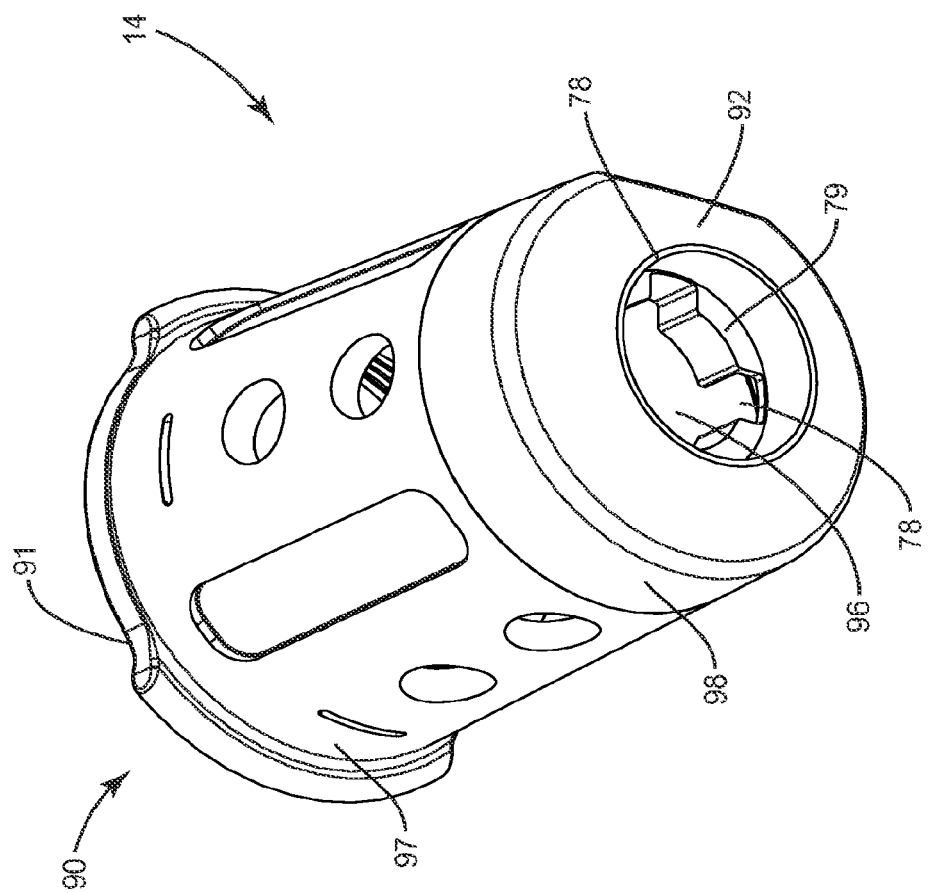
FIG. 6 is a perspective view of a distal side of a housing body.

The housing 14 extends around the planetary gear system 12 and portions of the input mechanism 11 and the output mechanism 13. The housing 14 may form the exterior of the instrument 10 as illustrated in FIG. 2, or may be an internal housing that is completely or partially covered by another element. As illustrated in FIGS. 3 and 6, the housing 14 includes a housing body 90 with an open proximal end 91 and a closed distal end 92. The distal end 92 includes an opening 96 through which the output mechanism 13 extends. The housing body 90 may be formed from a single piece of material, or may be formed from multiple pieces that are attached together. In one embodiment, the housing body 90 is constructed from a proximal section 97 and a distal section 98.

The housing body 90 includes an open interior 93 that receives the planetary gear system 12 and portions of the input and output mechanisms 11, 13. A shelf 99 is positioned axially inward from the proximal end 91 and extends radially inward from the side walls. The shelf 99 forms a seat for contacting against the proximal side 37 of the drive plate 30. The shelf 99 prevents the drive plate 30 from axially moving in a distal direction when a translational force is applied that overpowers the biasing member 70. A second shelf is positioned behind threads 95 that limits an extent of axial movement of the drive plate 30 in a proximal direction.

Indents 94 extend radially into the side wall of the housing body 90 at the proximal end 91. The indents 94 extend axially inward from the proximal end 91 and are spaced axially away from the shelf 99. The indents 94 are sized and shaped to receive the tabs 54 on the ring gear 50. The shapes and sizes of the proximal end 91 and the ring gear 50 provide for the ring gear 50 to fit within the interior 93 with the tabs 54 extending radially into the indents 94. This configuration provides for the housing body 90 to fixedly maintain the ring gear 50 (i.e., prevent the ring gear 50 to rotate within the interior 93). The proximal end 91 may also include threads 95.

The indents 94 may be sized to allow varying amounts of movement of the ring gear 50 relative to the housing body 90. The indents 94 as illustrated in FIG. 3 are purposefully oversized relative to the tabs 54 for the ring gear 50 to freely rotate a few degrees relative to the housing body 90 to help meshing of the gear 84 with the fingers 34. Another embodiment features the indents 94 closely sized relative to the tabs 54 to more rigidly hold the ring gear 50 relative to the housing body 90.

A cap 60 is sized to fit into and close the proximal end 91. The cap 60 includes a circular cross-sectional shape that substantially matches that of the proximal end 91. Threads 62 extend around the circumference and engage with the corresponding threads 95 to attach the cap 60 to the housing body 90. An aperture 61 may extend through a center of the cap 60 to allow for passage of the proximal section of the drive gear 20.

A torque adapter 65 may be attached to the cap 60. The adapter 65 includes a pair of flanges 66 that extend along and attached to opposing sides of the cap 60. A grip 67 may be positioned on the proximal end to facilitate handling and manipulating of the instrument 10. The grip 67 may include an annular shape to extend around the proximal end of the drive gear 20. The adapter 65 may include one or more attachment features 68 to attach to an exterior member (e.g., table, frame) to provide a counter-torque force to the instrument 10 when a rotational force is applied to the drive gear 20. FIG. 3 includes the attachment features 68 being cut-outs in the grip 68, although the features 68 may include other configurations and may be positioned at other locations along the adapter 65.

A first shaft 80 includes a proximal end 81 and a distal end 82. The distal end 82 includes a receptacle 85 for engaging with the section of the structural member 100 that is to be removed. The proximal end 81 includes a gear 84 with a number of radially-extending projections. The gear 84 is sized to engage with the fingers 34 that extend outward from the drive plate 30. The proximal end 81 and/or a surface of the gear 84 form a seat 83 that is contacted by the distal end 72 of the biasing member 70. The seat 83 may include an indent with an axially-extending rim that extends around the circumference that is sized to accommodate the distal end 72 of the biasing member 70.

Figure 8:
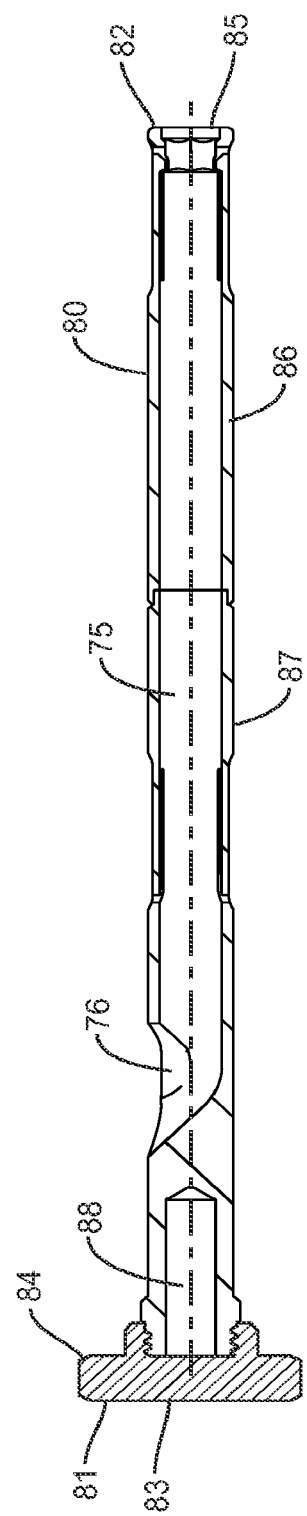
FIG. 8 is a sectional view of the first shaft cut along line VIII-VIII of FIG. 7.

The first shaft 80 also includes an interior bore 75 that receives the excess section of the structural member 100. The receptacle 85 at the distal end 82 forms a portion of the interior bore 75. The receptacle 85 may include flat sides to accommodate the polygonal cross-sectional shapes of the removed sections. The flat sides may extend a limited distance or an entire length of the interior bore 75. An outlet 76 is positioned along the interior bore 75 opposite from the receptacle 85. The outlet 76 provides for removing the removed sections from the first shaft 80. As illustrated in FIG. 8, the proximal end of the interior bore 75 is curved towards the outlet 76 to facilitate removal of the excess sections.

One or more flexible fingers 74 may be positioned along the length of the first shaft 80. The flexible fingers 74 include substantially U-shaped extensions that include an attached distal end and a free proximal end that is cut away from the first shaft 80. The free proximal ends of the fingers 74 may extend a limited distance into the interior bore 75. This configuration allows for the removed sections of the structural members 100 to move proximally through the interior bore 75 towards the outlet 76, but prevents movement in a distal direction where they may inadvertently escape from the distal end 82.

As illustrated in FIG. 8, the proximal end 81 of the first shaft 80 may also include an inlet 88. The inlet 88 is sized to receive the distal section of the post 35 when the first shaft 80 engages with the drive plate 30. FIG. 8 includes the inlet 88 having a back wall and being separated from the interior bore 75.

Figure 7:
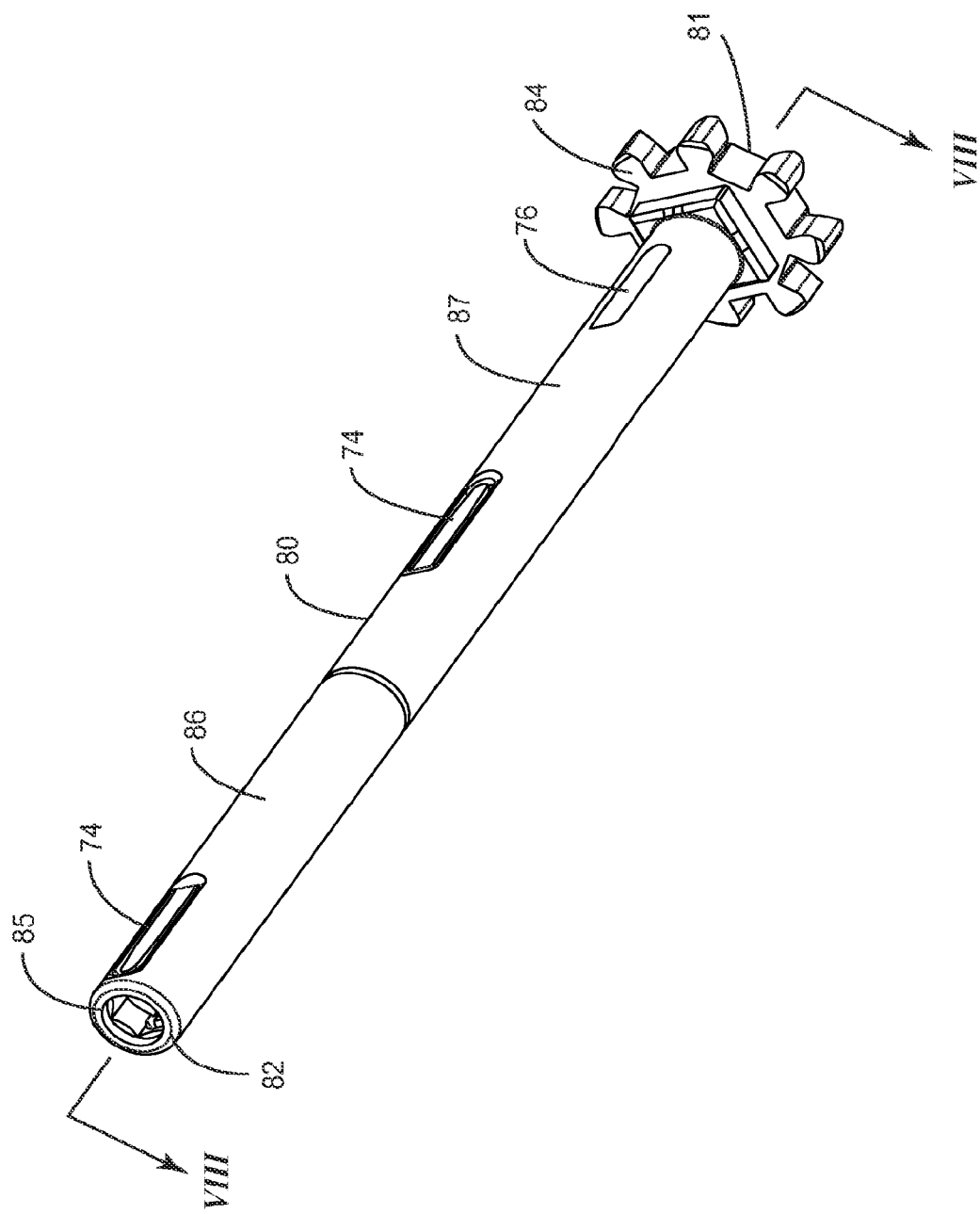
FIG. 7 is a perspective view of a first shaft.

The first shaft 80 may be formed as a single piece, or may include more than one piece. FIGS. 7 and 8 illustrate the first shaft 80 with a distal section 86 and a separate proximal section 87. Further, the gear 84 is a separate piece that is threaded onto the proximal end 81 of the proximal section 87.

The first shaft 80 extends through the opening 96 in the distal end 92 of the housing body 90. The first shaft 80 is axially movable within the opening 96 relative to the housing body 90. The gear 84 includes a larger cross-sectional size than the opening 96 to limit the extent of axial movement of the first shaft 80 relative to the housing body 90. In one embodiment, when the shaft 80 is biased in a distal direction by the biasing member 70, the shaft 80 is rotationally fixed by square edges near the gear 84 that mate with corresponding square edges within the interior 93 of the housing body 90.

The second shaft 110 is hollow and extends around the exterior of the first shaft 80. The second shaft 110 includes a distal end 111 and a proximal end 112. The distal end 111 includes one or more receptacles 113 on opposing sides that engage with a portion of the structural member 100 that remains within the patient. The proximal end 112 attaches to the housing body 90. The proximal end 112 may include radially-extending projections 114 that fit within gaps 78 formed between tabs 79 in the opening 96 in the housing body 90 (see FIG. 6). The proximal end 112 is attached to the housing body 90 and axially fixed relative to the housing body 90.

The first shaft 80 is axially movable within the second shaft 110. The first shaft 80 is positionable between a first extended position with the distal end 82 of the first shaft 80 extending outward beyond the distal end 111 of the second shaft 110. This positioning exposes the receptacle 85 at the distal end 82 for engaging with the section of the structural member 100 to be removed. The first shaft 80 is also positionable to a second, retracted position with the distal end 82 aligned with or recessed inward from the distal end 111 of the second shaft 110. This causes the one or more receptacles 113 at the distal end 111 of the second shaft 110 to be exposed The instrument 10 may be used in a number of different manners. One manner includes providing a rotational force to a section of the structural element 100 to secure the section within the patient. Using the example of the structural member 100 of FIG. 1, the instrument 10 may be attached to the set screw 100 for attaching it to the head 204 of the anchor 202. Specifically, the receptacle 85 at the distal end 82 of the first shaft 80 engages with the section 100b of the set screw. The instrument 10 is manipulated by the medical practitioner and aligned with the head 204 of the anchor 202. Once aligned, an axial force is applied to the instrument 10 towards the anchor 202. This axial force overcomes the force of the biasing member 70 and causes the first shaft 80 to axially move in the housing body 90. The axial movement causes the gear 84 to engage with the fingers 34 on the drive plate 30. Further, the post 35 on the drive plate 30 may be inserted into the inlet 88 in the distal end 82 of the first shaft 80. A rotational force is then applied to the input mechanism 11. The rotational force causes rotation of the drive gear 20 and planetary gear system 13. This rotation is transferred to the first shaft 80 which rotates the set screw into the head 204 of the anchor 202.

The instrument 10 may also be used to remove the excess section of the structural member 100. This process starts with first shaft 80 being in the extended position with the distal end 82 outward beyond the distal end 92 of the housing body 90. The receptacle 85 at the distal end 82 is attached to the section of the structural member 100 to be removed. The section to be removed may extend into the axial bore 75 in the first shaft 80 depending upon its length.

An axial force is applied to the instrument 10 to move the first shaft 80 to the retracted position. This axial movement causes the gear 84 to engage with the fingers 34 on the distal side 37 of the drive plate 30. The movement also causes the distal end 111 of the second shaft 110 to be exposed for attaching to a section of the structural member 100 that remains. In one embodiment, the one or more receptacles 113 at the distal end 111 are configured to attach to the elongated element 201.

A rotational force is applied to the proximal end 21 of the drive gear 20. This force causes rotation of the gears 40 around the posts 32 on the drive plate 30. The gears 40 engage with the ring gear 50 that is fixedly attached to the housing body 90. This causes the drive plate 30 to rotate within the housing body 90. The rotation of the drive plate 30 through the fingers 34 causes rotation of the first shaft 80 that is engaged with the section of the structural member 100 to be removed. The force applied to the drive gear 20 is multiplied by the planetary gear system 12 and distributed to the first shaft 80 to fracture the section from the remainder of the structural member 100. The attachment of the second shaft 100 with the remaining section of the structural member 100 prevents the "bucking" or "jerking" motion that may occur at the moment the section fractures from the remainder of the structural member 100.

The removed section of the structural member 100 may be captured in the interior bore 75. The instrument 10 may be manipulated to remove the section either through the receptacle 85 or through the outlet 76. Alternatively, the removed section may remain in the interior bore 75 as the instrument 10 is used to remove other sections of other structural members 100. The length of the interior bore 75 may be adequate to hold a number of removed sections.

The drive gear 20 may be configured to receive an input force from a variety of different methods. One type of drive force is provided through a rotational instrument that attaches to the proximal end 21 of the drive gear 20. The shape of the proximal end 21 is configured to engage with the rotational instrument. One type of rotational instrument is the POWEREASE™ Tapper-Driver available from Medtronic, Inc, of Minneapolis, Minn. The drive force may also be provided by the medical practitioner. The proximal end 21 may include a handle (not illustrated) and/or a roughened surface to facilitate contact by the medical practitioner who applies the input rotational force.

The instrument 10 may be used on a variety of different structural members 100. FIG. 1 illustrates the structural member 100 as a set screw for use with an anchor 202 for attaching a rod 201 to a bone 200. One type of set screw with first and second sections 100a, 100b designed for fracture and removal of the first section 100a is SET SCREW, BREAK-OFF available from Medtronic, Inc of Minneapolis, Minn.

Various other structural members 100 may be applicable for use with the instrument 10. Another embodiment features the structural member 100 being a screw with a break away drive head. The screw includes a threaded shaft with a first head section and a second head section. The first head section includes a receptacle for receiving a tool for initially attaching the screw to a bone. The first head section is configured with the second head section for removal after attachment to the bone. One example of a screw with a break away drive head is disclosed in U.S. Patent Application Publication No. 2007/0270859, herein incorporated by reference in its entirety.

The various structural members 100 may include a weakened fracture zone 101 positioned between the first and second sections 100a, 100b. The weakened fracture zone 101 may include a reduced cross-sectional size, a specific cross-sectional shape, a different material composition than the sections 100a, 100b, or various other mechanical aspects. The fracture zone 101 includes a smaller torsional strength than either of the sections 100a, 100b. This results in the structural member 100 fracturing in this zone for separating the first and second sections 100a, 100b.

FIG. 1 illustrates the instrument 10 used for during a vertebral surgical operation. The instrument 10 may also be used in various other surgical settings. Further, the instrument 10 may be used for cutting elongated elements 10 that are not attached to a patient.

Another embodiment of an instrument for removing sections of a structural member is disclosed in co-pending U.S. patent application Ser. No. 12/915,947 which is assigned to the same assignee as the present application.

The instrument 10 may be used during surgical procedures on living patients. The instrument 10 may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of removing a section of a structural member that is positioned in a patient comprising:
    attaching a receptacle of an output shaft to the section of the structural member that is to be removed;
    moving the output shaft axially relative to a planetary gear system and engaging the output shaft with the planetary gear system;
    rotating in a first direction an input member that is engaged with the planetary gear system and rotating the planetary gear system; and
    rotating the output shaft in the first direction through the planetary gear system and applying a force to the section of the structural member,
    wherein moving the output shaft axially relative to the planetary gear system and engaging the output shaft with the planetary gear system includes compressing a biasing member that biases the output shaft away from the planetary gear system and engaging a first member on the output shaft with a corresponding second member in the planetary gear system.

2. The method of claim 1, further comprising moving the output shaft axially and into a hollow shaft that extends outward away from the planetary gear system.

3. The method of claim 2, further comprising engaging a distal end of the hollow shaft that extends outward beyond the receptacle of the output shaft with a section of the structural member that remains within the patient.

4. The method of claim 1, wherein the planetary gear system is positioned within a housing.

5. The method of claim 4, wherein the input member is partially positioned in the housing and including an input portion that extends outward from the housing.

6. The method of claim 1, wherein the first member is a sun gear.

7. The method of claim 4, wherein output shaft is partially positioned in the housing and including a length to extend outward from the housing.

8. The method of claim 6, wherein the planetary gear system is positioned in the housing and the second member includes a plurality of planet gears that engage with and rotate around the sun gear.

9. The method of claim 8, wherein the sun gear is in communication with an annular gear that extends around the sun gear and the plurality of planet gears, the annular gear includes interior teeth that engage with the plurality of planet gears.

10. The method of claim 4, wherein the output shaft is movable relative to the housing from a first position with a proximal end of the output shaft spaced away from the planetary gear system and a second position with the proximal end spaced in closer proximity to the planetary gear system.

11. A method of removing a section of a structural member that is positioned in a patient comprising:
    providing a surgical instrument, the surgical instrument comprising:
        a housing;
        an input member partially positioned in the housing and including an input portion that extends outward from the housing, the input member being rotatable relative to the housing, the input member further including a sun gear;
        an elongated output shaft partially positioned in the housing and including a length to extend outward from the housing and include a receptacle configured to engage with the element, the elongated output shaft being rotatable relative to the housing;
        a planetary gear system positioned in the housing and including a plurality of planet gears that engage with and rotate around the sun gear, and an annular ring gear that extends around the sun gear and the plurality of planet gears and includes interior teeth that engage with the plurality of planet gears, the plurality of planet gears being rotatable relative to the housing and the ring gear being non-rotatable relative to the housing;
        the input member, the output shaft, and the planetary gear system being operatively connected for rotation of the input member in a first rotational direction resulting in rotation of the output shaft in the first rotation direction;
    attaching the receptacle of the output shaft to the section of the structural member that is to be removed;
    moving the output shaft axially relative to the planetary gear system and engaging the output shaft with the planetary gear system;
    rotating in the first direction the input member that is engaged with the planetary gear system and rotating the planetary gear system; and
    rotating the output shaft in the first direction through the planetary gear system and applying a force to the section of the structural member.

12. The method of claim 11, wherein moving the output shaft axially relative to the planetary gear system and engaging the output shaft with the planetary gear system includes compressing a biasing member that biases the output shaft away from the planetary gear system and engaging a first member on the output shaft with a corresponding second member in the planetary gear system.

13. The method of claim 11, further comprising moving the output shaft axially and into a hollow shaft that extends outward away from the planetary gear system.

14. The method of claim 13, further comprising engaging a distal end of the hollow shaft that extends outward beyond the receptacle of the output shaft with a section of the structural member that remains within the patient.

15. The method of claim 11, wherein the output shaft is movable relative to the housing from a first position with a proximal end of the output shaft spaced away from the planetary gear system and a second position with the proximal end spaced in closer proximity to the planetary gear system.

16. A system for removing a section of a structural member that is positioned in a patient comprising:
   a structural element comprising a shaft for engagement with tissue and an excess portion; and
   a surgical instrument comprising,
      a housing;
      an input member partially positioned in the housing;
      an elongated output shaft partially positioned in the housing opposite the input member, the output shaft configured to engage the structural element;
      a planetary gear system positioned in the housing and including a plurality of planet gears that engage with and rotate around a sun gear; and
      a biasing member that biases the output shaft away from the planetary gear system.

17. The system of claim 16, wherein the input member, the output shaft, and the planetary gear system are operatively connected for rotation of the input member in a first rotational direction resulting in rotation of the output shaft in the first rotational direction.

18. The system of claim 16, wherein the output shaft is movable relative to the housing from a first position with a proximal end of the output shaft spaced away from the planetary gear system and a second position with the proximal end spaced in closer proximity to the planetary gear system.

19. The method of claim 1, wherein the biasing member is a spring.

20. The method of claim 1, wherein the input member, the output shaft, and the planetary gear system are operatively connected for rotation of the input member in the first direction resulting in rotation of the output shaft in the first direction.

* * * * *